(12) United States Patent
Yl

(10) Patent No.: US 9,592,077 B2
(45) Date of Patent: Mar. 14, 2017

(54) CANNULA FOR PREVENTING SPRAYING OF LIQUID

(71) Applicant: Konyang University Industry-Academic Cooperation Foundation, Chungcheongnam-do (KR)

(72) Inventor: Jin Woong Yl, Daejeon (KR)

(73) Assignee: Konyang University Industry-Academic Cooperation Foundation, Nonsan-si, Chungecheongnam-do (KR)

( * ) Notice: Subject to any disclaimer, the term of this patent is extended or adjusted under 35 U.S.C. 154(b) by 346 days.

(21) Appl. No.: 14/306,568

(22) Filed: Jun. 17, 2014

(65) Prior Publication Data

US 2014/0371681 A1    Dec. 18, 2014

(30) Foreign Application Priority Data

Jun. 18, 2013    (KR) ........................ 10-2013-0069825

(51) Int. Cl.
*A61M 5/32*    (2006.01)
*A61B 17/34*    (2006.01)

(52) U.S. Cl.
CPC .. *A61B 17/3462* (2013.01); *A61B 2017/3437* (2013.01); *A61B 2017/3484* (2013.01); *A61B 2017/3492* (2013.01)

(58) Field of Classification Search
CPC ........ A61B 2017/3484; A61B 17/3423; A61B 17/3462; A61B 17/3498; A61B 2017/3437; A61B 2017/3492
USPC ......................................................... 604/175
See application file for complete search history.

(56) References Cited

U.S. PATENT DOCUMENTS

| | | | | |
|---|---|---|---|---|
| 5,694,922 A | * | 12/1997 | Palmer | A61M 39/26 128/202.27 |
| 8,262,568 B2 | * | 9/2012 | Albrecht | A61B 17/0293 600/206 |
| 2006/0217665 A1 | * | 9/2006 | Prosek | A61B 17/3421 604/167.02 |

* cited by examiner

*Primary Examiner* — Jason Flick
(74) *Attorney, Agent, or Firm* — Rabin & Berdo, P.C.

(57) ABSTRACT

A cannula for preventing spraying of liquid is disclosed. The cannula includes a support tube partially inserted into a human body to guide a surgical instrument to an inside of the human body and a handle integrally formed with the support tube to allow the surgical instrument to be in and out of the human body, wherein the handle further includes a plurality of seal plates coupled to an inside thereof to prevent spraying of liquid onto an operator by an internal pressure of the human body and an outlet formed at a side surface thereof to reduce an internal pressure of the handle to atmospheric pressure.

5 Claims, 7 Drawing Sheets

CANNULA FOR PREVENTING SPRAYING OF LIQUID

BACKGROUND OF THE INVENTION

Field of the Invention

The present invention relates to a cannula for preventing spraying of liquid and, more particularly, to a cannula for preventing spraying of liquid that may prevent liquid of a subject undergoing medical treatment from spraying onto an operator by discharging internal pressure of the cannula to air.

Description of the Related Art

In general, medical cannulas are partially inserted into incised skin to secure an incision and in this state, surgical instruments are inserted into a cannula to perform medical treatment.

Such a cannula secures a state where the skin is incised during medical treatment for rotator cuff surgery, Bankart repair, long head of Biceps Tendon surgery, glenohumeral joint surgery, or the like, or during various medical treatments using a joint endoscope for knee bones, semilunar cartilage, cruciate ligaments, and the like.

In addition, a cannula is fixedly inserted partially into the human body and medical instruments are inserted into the cannula to perform medical treatment.

A conventional cannula 10 has a structure as illustrated in FIG. 1 in which two fixing plates 13 are integrally formed at opposite ends of a support tube 12.

Thus, when the cannula 10 is inserted into the human body after skin is incised, each fixing plate 13 is fixed flexibly in contact with inner and outer sides of the skin of the human body.

However, it is impossible to change the shape of the cannula 10 and thus a suitable cannula has to be used according to skin or muscle thickness of a subject undergoing medical treatment.

In addition, the cannula 10 has a drawback in that, when surgical instruments are inserted into the cannula 10 to perform an operation, liquid sprays out via a gap therebetween onto an operator by internal pressure of the body of a subject undergoing medical treatment, which may cause medical accidents.

SUMMARY OF THE INVENTION

Therefore, the present invention has been made in view of the above problems, and it is an object of the present invention to provide a cannula for preventing spraying of liquid that includes a plurality of seal plates to prevent liquid of a subject undergoing medical treatment from spraying onto an operator.

It is another object of the present invention to provide a cannula for preventing spraying of liquid that may prevent liquid of a subject undergoing medical treatment from spraying onto an operator by discharging internal pressure of the cannula to air.

It is further another object of the present invention to provide a cannula for preventing spraying of liquid that may be supported easily according to skin, muscle or bone thickness of various subjects undergoing medical treatment.

In accordance with an aspect of the present invention, the above and other objects can be accomplished by the provision of a cannula for preventing spraying of liquid that includes a support tube partially inserted into a human body to guide a surgical instrument to an inside of the human body and a handle integrally formed with the support tube to allow the surgical instrument to be in and out of the human body, wherein the handle further includes a plurality of seal plates coupled to an inside thereof to prevent spraying of liquid onto an operator by an internal pressure of the human body and an outlet formed at a side surface thereof to reduce an internal pressure of the handle to atmospheric pressure.

The outlet may be configured to be in communication with a rear space of the outermost seal plate among the seal plates and may be provided with a discharge guide tube rotatably coupled thereto to guide discharge of liquid of a subject undergoing medical treatment.

Each seal plate may be provided at a central portion thereof with an incision portion partially formed through which the surgical instrument is inserted.

The support tube or the handle may be further provided with an auxiliary tube connected thereto through which, during medical treatment, medication or saline is supplied to the inside of the body of a subject undergoing the medical treatment.

The support tube may be fixed to skin, muscle or bone of the human body through a fixing plate integrally formed at an end thereof and a pressurizing plate screw-coupled to an outer circumferential surface thereof.

The fixing plate may have an upwardly curved edge.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
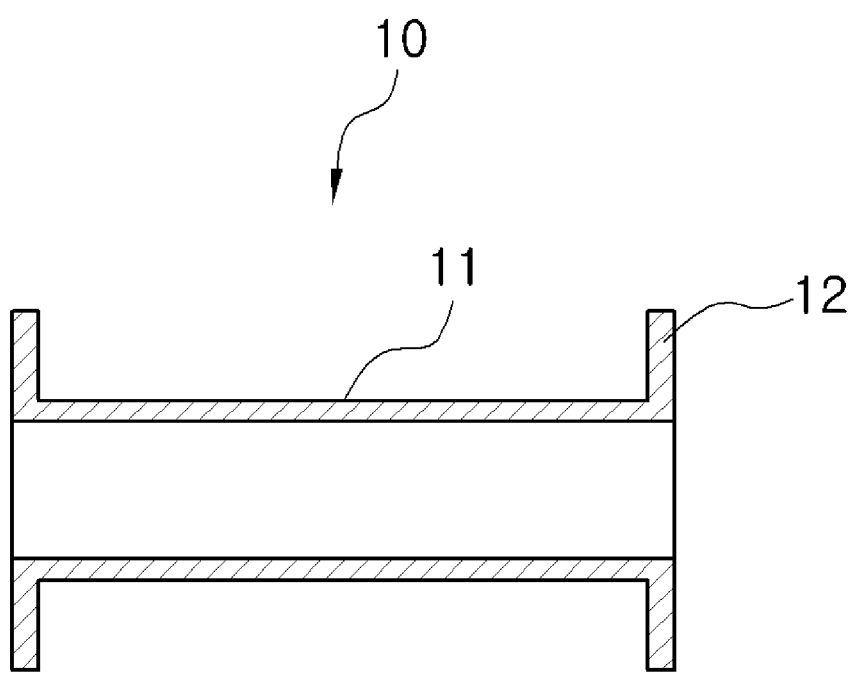
FIG. 1 is a sectional view of a conventional cannula.

As the invention allows for various modifications and numerous embodiments, particular embodiments will be illustrated in the drawings and described in detail in the detailed description. However, this is not intended to limit the scope of the invention, and it is to be understood that all changes, equivalents, and substitutes are within the scope and spirit of the present invention.

In addition, in description of the present invention, detailed explanations of the related art are omitted when it is deemed that they may unnecessarily obscure the essence of the invention.

In addition, it will be understood that when an element is referred to as being "coupled" or "connected" to or "in communication with" another element, it can be directly coupled or connected to or directly in communication with the other element. However, unless otherwise stated, it will be understood that an element may be coupled or connected to or in communication with another element with intervening elements therebetween.

Hereinafter, a cannula for preventing spraying of liquid according to the present invention will be described in detail with reference to the accompanying drawings.

The term "liquid" as used herein denotes blood, saline, medications, and the like.

Figure 2:
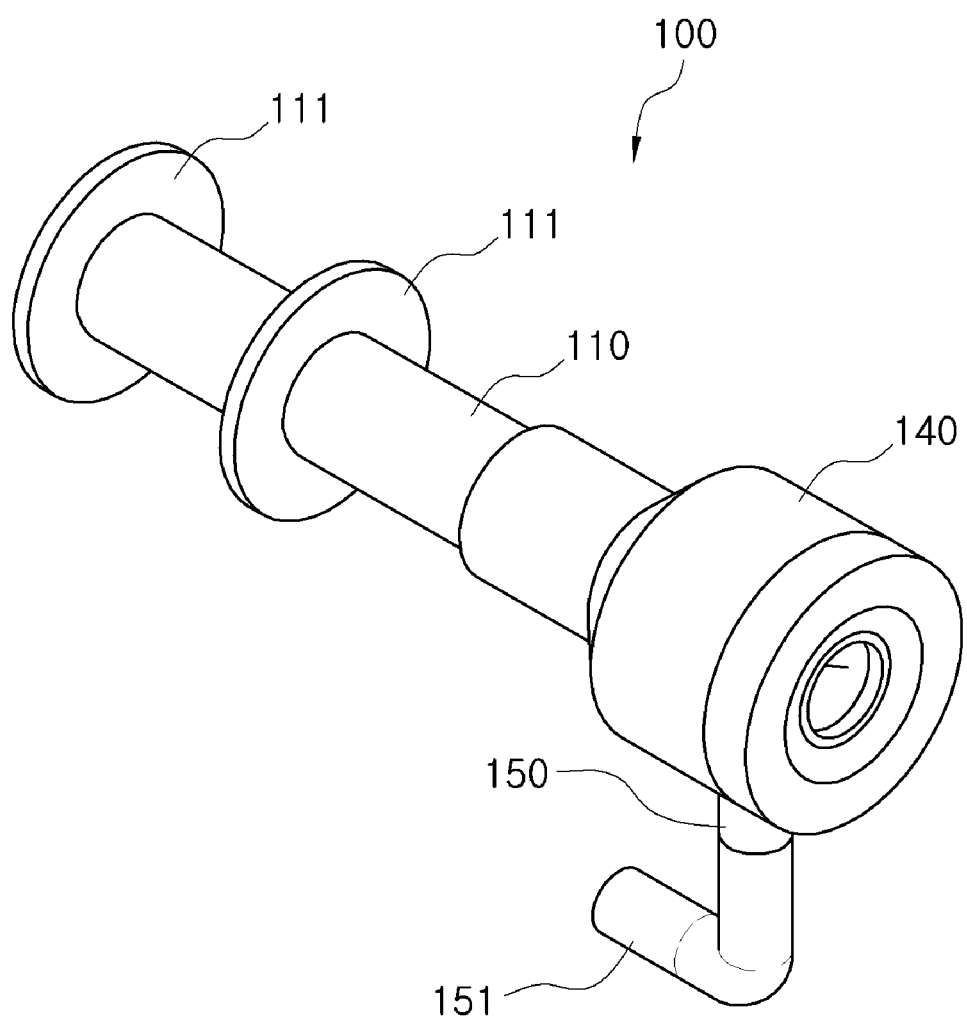
FIG. 2 is a perspective view of a cannula for preventing spraying of liquid according to a first embodiment of the present invention.
Figure 3:
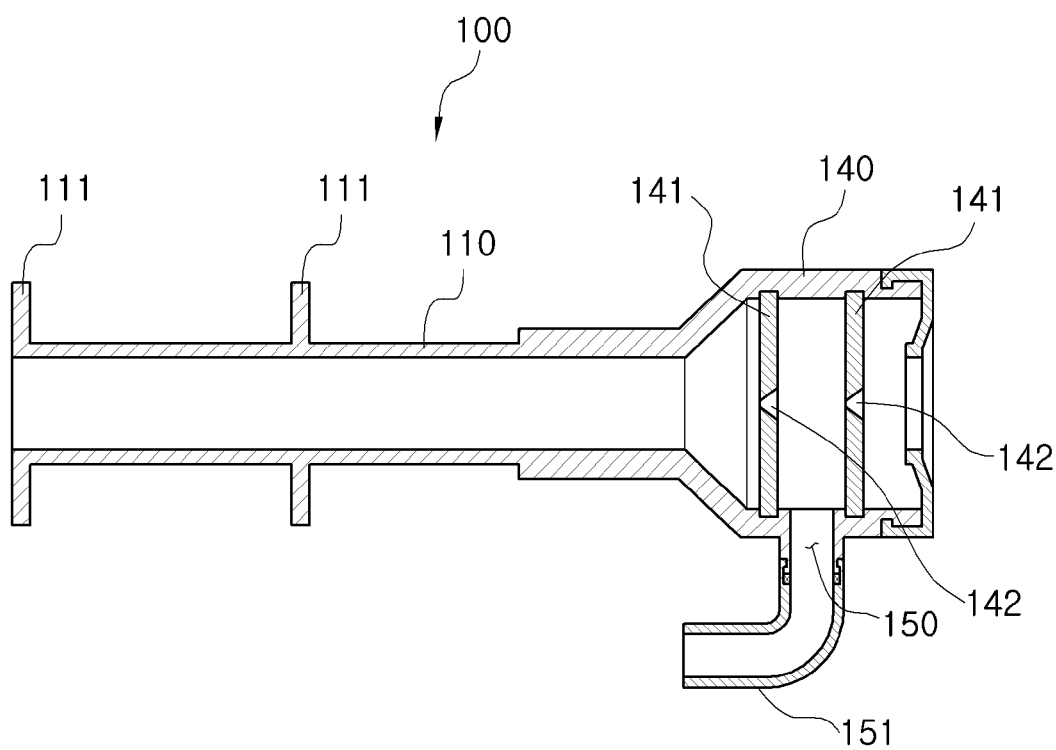
FIG. 3 is a sectional view of the cannula of FIG. 2.

FIG. 2 is a perspective view of a cannula 100 for preventing spraying of liquid according to a first embodiment of the present invention. FIG. 3 is a sectional view of the cannula 100 of FIG. 2.

As illustrated in FIGS. 2 and 3, the present invention relates to the cannula 100 for preventing spraying of liquid that prevents liquid of a subject undergoing medical treatment from spraying onto an operator.

The cannula 100 broadly consists of two parts: a support tube 110 and a handle 140.

The support tube 110 is partially inserted into the body of a subject undergoing medical treatment to guide a surgical instrument to the inside of the human body.

The handle 140 is integrally formed with the support tube 110 to allow surgical instruments to be in and out of the human body.

The handle 140 has a greater outer diameter than the support tube 110 so that an operator can easily grab the handle 140 and also has a greater inner diameter than the support tube 110 to reduce internal pressure thereof.

In addition, the handle 140 includes a plurality of seal plates 141 coupled to the inside thereof to prevent liquid of a subject undergoing medical treatment from spraying onto an operator by internal pressure of the human body.

In addition, the handle 140 is provided with an outlet 150 coupled to a side surface thereof so as to reduce the internal pressure to atmospheric pressure.

In this regard, although FIG. 3 illustrates two seal plates 141 for prevention of spraying of liquid onto an operator by internal pressure of the cannula 100, various modifications, such as one seal plate or three or four seal plates coupled to each other, are possible.

Each seal plate 141 is provided at a central portion thereof with an incision portion 142 through which a surgical instrument is inserted. In another embodiment, the incision portion 142 may include incision portions formed by radially incising the seal plate 141.

The outlet 150 is configured to prevent liquid from spraying onto an operator by reducing the internal pressure of the cannula 100 to atmospheric pressure and to discharge the liquid to the outside.

The outlet 150 is configured to be in communication with a space between the seal plates 141. When the number of the seal plates 141 is 3, 4 or 5, the outlet 150 is configured to be in communication with a rear space of the outermost seal plate 141.

In addition, at least two outlets 150 may be formed according to the number of the seal plates 141.

In addition, the outlet 150 is provided with a discharge guide tube 151 rotatably coupled thereto to prevent the discharge guide tube 151 from being twisted by rotation and to guide the discharged liquid to a storage vessel.

In addition, the support tube 110 is provided with two fixing plates 111 so as to be fixed to the skin, muscle or bone of a subject undergoing medical treatment.

Figure 4:
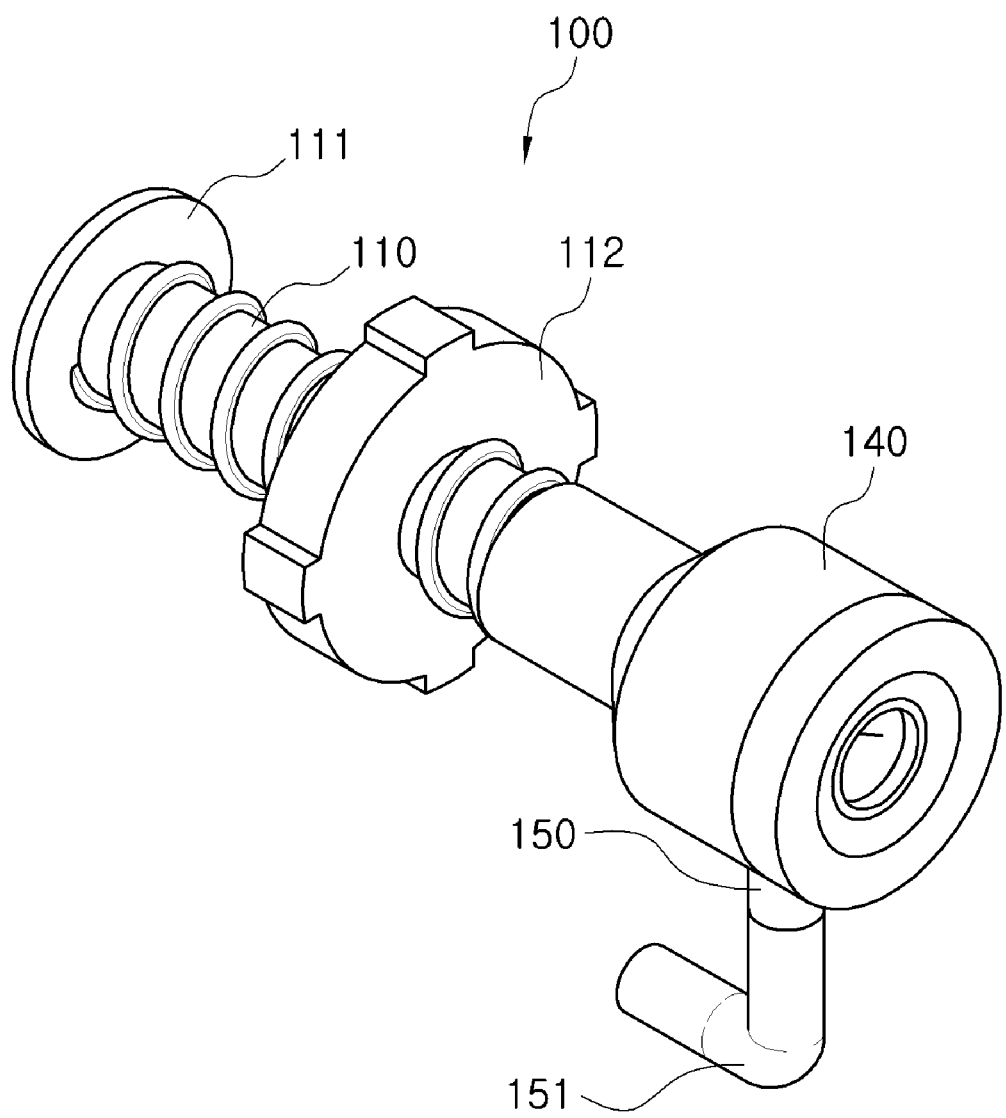
FIG. 4 is a perspective view of a cannula for preventing spraying of liquid according to a second embodiment of the present invention.
Figure 5:
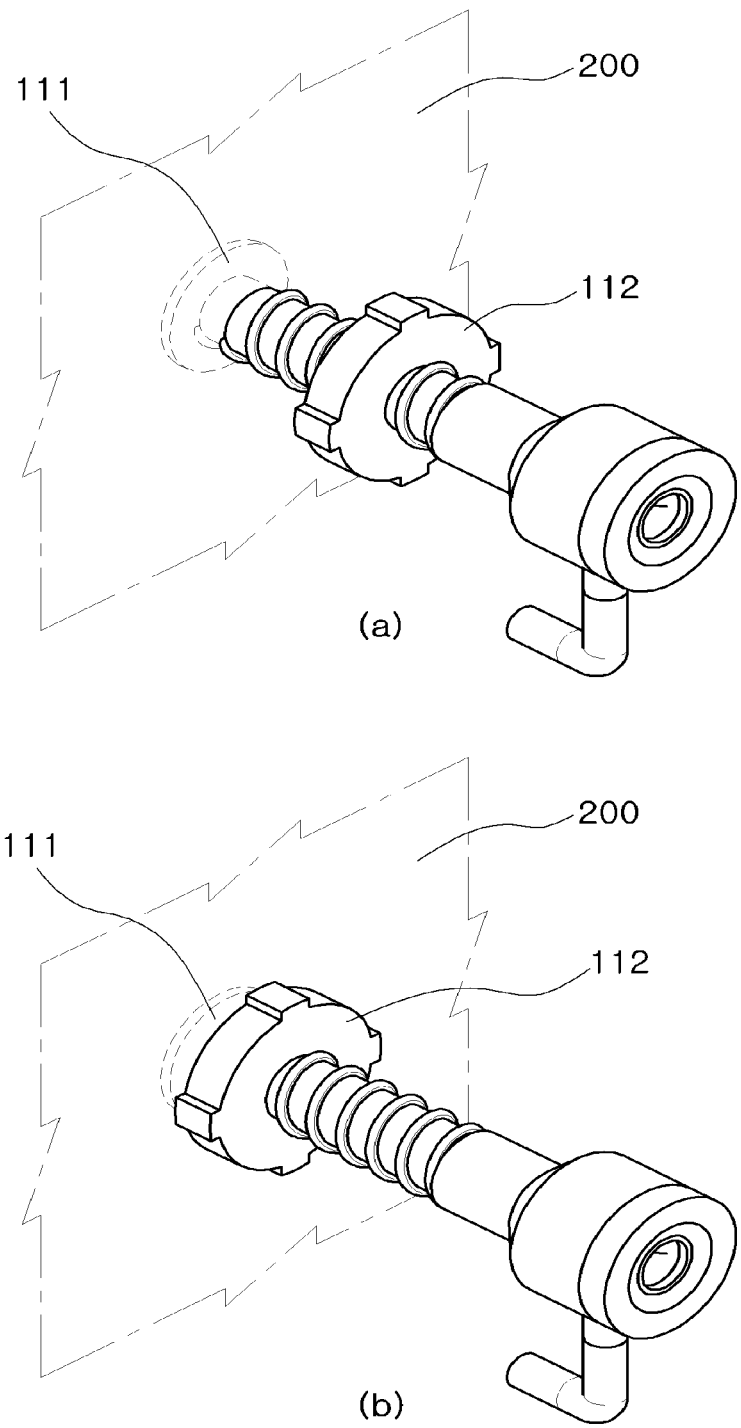
FIG. 5 illustrates operation of the cannula of FIG. 4.

FIG. 4 is a perspective view of a cannula 100 for preventing spraying of liquid according to a second embodiment of the present invention. FIGS. 5(a) and 5(b) are views illustrating operation of the cannula 100 of FIG. 4.

As illustrated in FIG. 4, the support tube 110 according to the second embodiment further includes a fixing plate 111 integrally formed at an end thereof and a pressurizing plate 112 that is screw-coupled to an outer circumferential surface thereof.

The support tube 110 is configured to enable easy fixing of the cannula 100 regardless of different skin, muscle or bone thicknesses of respective subjects undergoing medical treatment.

As illustrated in FIGS. 5(a) and 5(b), when a skin 200 is incised and the pressurizing plate 112 is pressed so as to contact the outside of the skin 200 in a state of inserting the fixing plate 111 into the skin 200, the support tube 110 of the cannula 100 may be stably fixed to the skin 200 of a subject undergoing medical treatment.

In addition, since the pressurizing plate 112 presses the outside of the skin 200, blooding of the incised skin 200 is stopped and leakage of liquid to the outside of the incised skin 200 may also be prevented.

Figure 6:
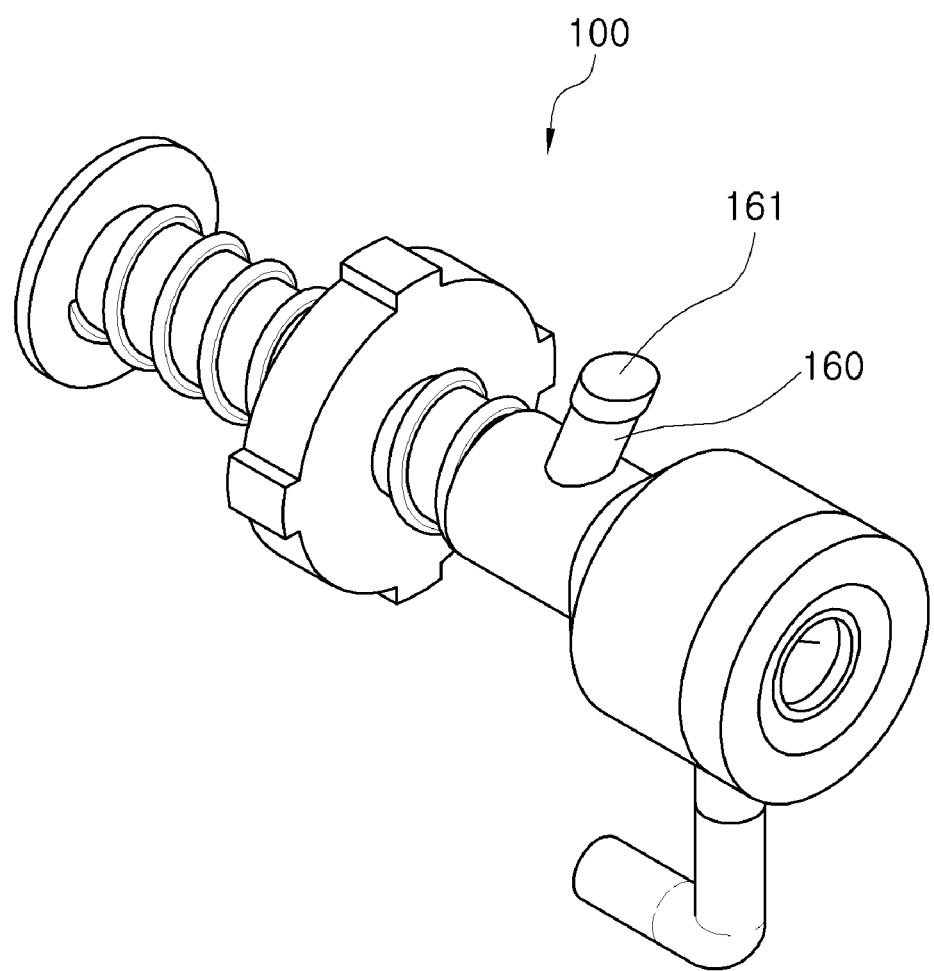
FIG. 6 is a perspective view of a cannula for preventing spraying of liquid according to a third embodiment of the present invention.

FIG. 6 is a perspective view of a cannula 100 for preventing spraying of liquid according to a third embodiment of the present invention.

As illustrated in FIG. 6, the cannula 100 according to the third embodiment has the same basic structure as that of the cannula 100 according to the second embodiment, except that the support tube 110 or the handle 140 is further provided with an auxiliary tube 160 connected thereto through which medication is supplied to the inside of the body of a subject undergoing medical treatment or saline is supplied to maintain internal pressure of liquid in the human body.

The auxiliary tube 160 is configured to be in communication with the inside of the support tube 110 or the handle 140. In the present embodiment, the auxiliary tube 160 is configured to be in communication with the support tube 110.

The auxiliary tube 160 may be provided with a stopper 161 to close the auxiliary tube 160 when not in use so as to prevent bacteria from permeating into the cannula 100. When the auxiliary tube 160 is used, the stopper 161 may be removed.

Figure 7:
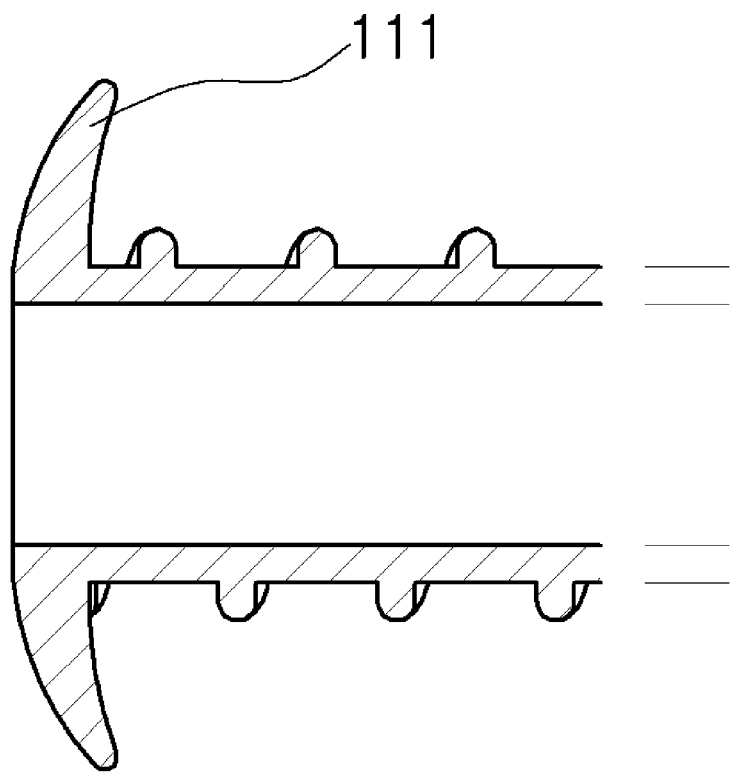
FIG. 7 is a sectional view illustrating another example of a fixing plate, according to a fourth embodiment of the present invention.

FIG. 7 is a sectional view illustrating another example of the fixing plate 111, according to a fourth embodiment of the present invention.

As illustrated in FIG. 7, the fixing plate 111 has an upwardly curved edge.

Such configuration enables easy insertion of the fixing plate 111 into an incision portion of the body of a subject undergoing medical treatment and may prevent escape of the fixing plate 111 from the incision portion such that the fixing plate 111 contacts the inside of the skin after insertion and is supported and thus acts as an anchor.

As is apparent from the above description, according to a cannula for preventing spraying of liquid, during medical treatment, spraying of liquid of a subject undergoing medical treatment onto an operator may be prevented using a plurality of seal plates and an outlet and thus operation delay and emergency situations may be prevented.

In addition, by using a pressurizing plate to press the skin of a subject undergoing medical treatment, the cannula may be easily fixed regardless of skin, muscle or bone thickness of various subjects undergoing medical treatment. In addition, as secondary effects, blooding of an incised skin may be stopped by pressing the skin using the pressurizing plate.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A cannula for preventing spraying of liquid, the cannula comprising:
 a support tube capable of partially inserting into a human body to guide a surgical instrument to an inside of the human body; and
 a handle integrally formed with the support tube to allow the surgical instrument to be in and out of the human body,
 wherein the handle comprises a plurality of seal plates coupled to an inside thereof to prevent spraying of liquid onto an operator by an internal pressure of the human body and an outlet formed at side surface thereof,
 wherein each seal plate is provided at a central portion thereof with an incision portion partially formed through which the surgical instrument is inserted, and
 wherein the outlet is disposed between two adjacent seal plates of the plurality of seal plates to reduce an internal pressure of the handle between the two adjacent seal plates to atmospheric pressure.

2. The cannula according to claim 1, wherein the handle has a first end which faces the support tube and a second end opposite to the first end,
 wherein the two adjacent seal plates are two nearest seal plates to second end among the plurality of seal plates, and
 wherein the outlet is configured to be in communication with a space between the two adjacent seal plates, and the outlet is provided with a discharge guide tube rotatably coupled thereto to guide discharge of liquid of a subject undergoing medical treatment.

3. The cannula according to claim 1, wherein the support tube or the handle is further provided with an auxiliary tube connected thereto through which, during medical treatment, medication or saline is supplied to the inside of the body of a subject undergoing the medical treatment.

4. The cannula according to claim 1, wherein the support tube is capable of being fixed to skin, muscle or bone of the human body through a fixing plate integrally formed at an end thereof and a pressurizing plate screw-coupled to an outer circumferential surface thereof.

5. The cannula according to claim 4, wherein the fixing plate has an upwardly curved edge.

* * * * *